United States Patent [19]

Stevens et al.

[11] Patent Number: 4,751,004

[45] Date of Patent: Jun. 14, 1988

[54] LIQUID CHROMATOGRAPHIC METHOD AND APPARATUS WITH A PACKED TUBE MEMBRANE DEVICE FOR POST-COLUMN DERIVATIZATION/SUPPRESSION REACTIONS

[75] Inventors: Timothy S. Stevens; Gary L. Jewett; Robert A. Bredeweg, all of Midland, Mich.

[73] Assignee: The Dow Chemical Company, Midland, Mich.

[21] Appl. No.: 858,077

[22] Filed: Apr. 25, 1986

Related U.S. Application Data

[63] Continuation of Ser. No. 605,949, May 1, 1984, abandoned, which is a continuation of Ser. No. 300,143, Sep. 18, 1981, abandoned.

[51] Int. Cl.[4] .............................................. B01D 15/08
[52] U.S. Cl. ...................................... 210/659; 422/70
[58] Field of Search ............... 422/70; 210/656, 502.1, 210/317, 658, 456, 198.2, 659; 436/161; 73/61.1 C

[56] References Cited

U.S. PATENT DOCUMENTS

| | | | |
|---|---|---|---|
| 3,186,941 | 6/1965 | Skiens | 210/638 |
| 3,228,876 | 1/1966 | Mahon | 210/638 |
| 3,256,678 | 6/1966 | Bertin et al. | 210/456 X |
| 3,598,728 | 8/1971 | Bixler et al. | 210/22 |
| 4,247,393 | 1/1981 | Wallace | 210/502.1 X |
| 4,265,634 | 5/1981 | Pohl | 210/656 |
| 4,474,664 | 10/1984 | Stevens et al. | 210/656 |

FOREIGN PATENT DOCUMENTS 1258631 5/1962 Fed. Rep. of Germany .

OTHER PUBLICATIONS

Abstract B. 26 from the McSAC-Conference of Jul. 20–26, 1980, Lancaster, England, "Dispersion in Tubes Under Conditions Used in Flow Injection Analysis," J. M. Reijn et al.
Analytica Chimica Acta. 123 (Jan., 1981), 229–337, "Dispersion in Open Tubes and Tubes Packed with Large Glass Beads," Reijn et al.
Analytica Chimica Acta, 126 (May, 1981), 1–13, "Transport Phenomena in Flow Injection Analysis Without Chemical Reaction," Reijn et al.
Savage, W. F., Saline Water Conversion Report for 1970–1971, pp. 96–98.

Primary Examiner—Frank Spear
Attorney, Agent, or Firm—Burke M. Halldorson; Timothy S. Stevens

[57] ABSTRACT

Packing tube membranes or membrane channels for Ion Chromatography with inert or charged ion exchange beads greatly increases overall suppressor efficiency. The length of membrane required is reduced, e.g. from 20 feet to 5 feet and bandspreading is reduced from 870 $\mu l$ to 200 $\mu l$. This significant increase in efficiency is attributed to the mixing action of the packing on the flow stream which results in convective radial transport much more rapid than the diffusion controlled transport observed in unpacked membranes. The technique is also described for developing more efficient liquid chromatographic post-column reactors for adding reagent to the column effluent to increase detection sensitivity.

30 Claims, 3 Drawing Sheets

LIQUID CHROMATOGRAPHIC METHOD AND APPARATUS WITH A PACKED TUBE MEMBRANE DEVICE FOR POST-COLUMN DERIVATIZATION/SUPPRESSION REACTIONS

CROSS REFERENCE TO RELATED APPLICATION

This is a continuation of application Ser. No. 605,949, filed May 1, 1984, which is a continuation of application Ser. No. 300,143, filed Sept. 18, 1981, both abandoned.

BACKGROUND OF THE INVENTION

In conventional liquid chromatography, using high quality components, extra column band spreading is usually on the order, e.g., of about 50–100 μl or less and thus generally is not significantly detrimental to the analysis. This holds true also for the case of high performance analytical columns. However, where the additional element of a post-column reactor or suppressor device is used between the column and detector, some greater amount of band spreading is introduced. In the case of high performance analytical columns, for example, those having a resolution efficiency of about 20,000 theoretical plates or greater, such additional band spreading can be detrimental in its effect on detection sensitivity, and/or as a primary cause of sample interferences. The present invention, in this respect, provides a practical and effective solution for controlling sample band spreading in practicing post column derivatization and suppression reactions in the field of liquid chromatography.

Specifically, among prior liquid chromatographic apparatus and method which may be significantly improved by the teachings of this invention is the apparatus used in conventional Ion Chromatography, e.g., as described by Small, "Applications of Ion Chromatography in Trace Analysis", Academic Press, New York, Chapter in "Trace Analysis", Editor James F. Lawrence (In Press); (see also, U.S. Pat. No. 3,920,397). Ion Chromatography is an analysis method which is based on a post-column suppression reaction. In this respect, liquid sample placed on an ion exchange analytical column is displaced by an electrolyte eluent or mobile phase, and elutes in a highly conductive eluent background solution which interferes with sensitive conductimetric detection of the sample ions. A "suppressor" column comprising a bed of ion exchange particles is thus placed between the analytical column and detector, and is used to selectively convert the electrolyte eluent to, e.g., deionized water or other weakly ionized background solution in which the sample ions can be sensitively detected. However, because of detrimental band spreading generally only relatively small suppressor columns are useful in Ion Chromatography, and these undesirably require frequent regeneration or replacement, as well as place other critical restrictions on the method (such as the usable strength of the eluent solution). In addition, even with these small suppressor columns, band spreading is nevertheless frequently on the order of, e.g., 300 μl, or in an amount which can degrade the resolution efficiencies of high performance chromatographic columns.

The prior art has also developed a considerable variety of chemical reagents of a nature generally considered suitable for addition to liquid chromatographic effluent to enhance the detection sensitivity of eluted sample bands with reference to a specific detector, usually a photometer or fluorometer, but including other detectors; or to enhance their sensitivity with respect to interfering bands which overlap bands of interest. Various reagents and reagent reactions specifically contemplated as useful for liquid chromatography, for example, are described in some detail by Snyder et al., *Introduction to Modern Liquid Chromatography*, 2nd Ed. (1979) 740–746, herein incorporated by reference. Also incorporated herein by reference to illustrate this state of the art are the reagents and reagent reactions taught by Gfeller et al., *Journal of Chromatography*, 142 (1977), pp. 271–281; Frei et al. and Jupille, *Journal of Chromatographic Science*, Vol. 17, March, 1979, pp. 152–159 and 160–167, respectively; and Vance Nau et al., *Analytical Chemistry*, Vol. 51, No. 3, March 1979, pp. 424–428. In spite of the longtime availability of the above and like prior art teachings, however, reagent addition chemistry has only infrequently been applied to past liquid chromatographic practices. For example, it is stated:

"Although the use of such reaction techniques after column chromatographic separation has been known for more than a decade [ ] little has appeared in relation to modern HPLC. One reason is the many technical problems [ ] that still have to be solved" (Gfeller et al., p. 271).

-and-

"The adaptation of reaction detection to modern LC columns requires careful attention to [ ] the design of equipment, because extra column effects can be serious. For these reasons reaction detectors have so far found rather limited use in modern LC." (Synder et al., p. 740).

Among the above-referenced "extra column effects" is frequently detrimental band spreading or band broadening. For example, Frei et al., state: "the construction of proper reaction detectors comprises a constant struggle against band broadening"; and Jupille states, in respect to reagent addition methods, "a need for hardware modification (with attendant loss in flexibility); and [ ] a risk of band broadening due to post-column mixing volume resulting in loss of resolution."

Accordingly, it is a primary objective of this invention to provide liquid chromatographic apparatus and methods in which improved utility and flexibility are achieved in the practice and implementation of post column suppression and/or reagent addition reactions. It is particularly an object of the invention to provide such liquid chromatographic apparatus and method in which band spreading inherently produced by a post column suppressor or reactor device is acceptably controlled, and wherein the primary utility of producing an effective suppression or reagent addition reaction is simultaneously and effectively accomplished.

THE INVENTION

The invention is basically the discovery that packings or equivalent structures which produce radial mixing in channels can be used in combination with membranes to develop suppressor devices for Ion Chromatography, and reagent addition devices for liquid chromatographic post column reactions in which band spreading at detrimental levels is effectively controlled.

In respect to differences over the prior art, the use of the membrane by itself is not new. Flat membranes, for example, have been suggested in the past for applications similar to the invention. The invention, however, is in the combination of the packing and the membrane which has not been described. Additionally, in terms of technical differences, devices based on prior flat membrane designs have in the past been of a type particularly ineffectual in controlling band spreading occurring at highly detrimental levels. These devices, therefore, are not comparable to the invention in terms of critical utility.

Another area of prior art over which the invention is defined concerns devices known as the "hollow fiber suppressor" and "hollow fiber" post-column reactor. These are described respectively, in U.S. Patent Application Ser. No. 429,357, by Stevens et al., entitled "Ion Analysis Method and Apparatus", originally filed Jan. 16, 1980, now U.S. Pat. No. 4,474,664; and U.S. patent application, Ser. No. 465,977, by Davis, entitled "Liquid Chromatographic Method and Apparatus with Hollow Fiber Device For Post Column Derivatization", originally filed Sept. 2, 1980 (now U.S. Pat. No. 4,448,691).

The most apparent difference between the invention and the above prior art, is again that the invention is the combination of the packing plus the membrane, whereas the former devices do not contemplate the combination, but the use of the membrane alone. The differences in utility, however, are very significant to the practitioners of liquid chromatography. This is not to say that the prior device of the hollow suppressor, for example, is an unimportant development since it overcomes many of the published difficulties associated with a packed bed form of suppressor column. However, these benefits are achieved only at the expense of a penalty in band spreading and this is the problem the present invention solves which makes the earlier membrane technology significantly more valuable to liquid chromatographic analysis.

In specific reference to reagent addition reactions, as opposed to the above discussed suppression reactions, the technical contributions of the invention are viewed somewhat differently. Here, oftentimes, the most important benefit is that the invention advantageously permits the liquid chromatographic practitioner to select and use membranes and membrane structures previously thought to have little or no utility for post column reagent addition purposes. In this respect, because of severe band spreading, only very fine hollow fiber strands are taught to have utility for use in prior liquid chromatographic reactor devices (such as constructed by Davis, U.S. Pat. No. 4,448,691). Only a relatively few of the known membrane materials are thus, in fact, available in the form critically required by Davis. In contrast, the invention is not limited to the narrow field of hollow fibers in developing optimum membranes for liquid chromatographic reagent addition purposes, since the invention is not limited to a hollow fiber geometry in order to control detrimental band broadening.

TERMS

"Analytical Column" means any suitable chromatographic stationary phase usually on supports such as particles, but also other supports, e.g., capillaries and the like, useful in performing liquid chromatographic separations.

"Eluent" means a liquid mobile phase suitable for use with the analytical column for performing liquid chromatographic separations.

"Hollow fiber" means an extremely small tube or fiber having an internal diameter of between about 20–1,000 microns.

"Membrane" means a material which will selectively exchange ions or permeate a reagent while rejecting or retaining a detectably useful amount of sample of interest.

"regenerant" or "Regenerant Solution" means ions which are of a kind useful for regenerating an ion-exchange membrane so that said membrane can chemically convert electrolyte eluent into deionized water or to another less ionized or weakly ionized form in order to sensitively detect sample of interest.

"Reagent" means a chemical species or combination of species which are of a kind that, when introduced through a membrane into chromatographic analytical column effluent, react chemically, directly or indirectly, with a sample species of interest or an interfering sample species less than perfectly resolved with respect to a sample species of interest, for the purpose of enhancement of the sensitivity of detection of said species of interest, or a monitored proportional derivative thereof.

"Packing means" refers most specifically to particles arranged in a matrix which is liquid porous. In its broadest sense it is meant to include equivalents such as a small chain or configured wire on a sintered or open cellular matrix element added to the bore of a hollow fiber or tube or channel for the purposes of duplicating the mixing effect of a particle matrix therein according to the invention, and which otherwise is nondetrimental to the purposes of the invention.

"Reactor" means a liquid chromatographic device for post-column reactions by reagent addition, and is additionally meant to include, generically, post-column suppressor devices for performing the suppression reaction in Ion chromatography.

The term "reactor" also means a device used for the above post-column reactions without the use of an analytical column as demonstrated in Example 1 below wherein the liquid passed through the reactor is termed the eluent.

"Flow-through Channel" means and includes multiple channels as may be constructed, e.g., by connecting multiple tube membranes in parallel.

"Selectively exposed" refers to a membrane in which one surface or surface portion thereof is exposed to a flow-through channel for contact with chromatographic effluent, and its opposite surface or surface portion is isolated from the channel and effluent by the thickness of the membrane.

GENERAL DESCRIPTION OF THE INVENTION

The invention as it relates to liquid chromatographic apparatus comprises a liquid chromatographic reactor in which there is included a flow-through channel adapted for passing through liquid chromatographic effluent to a detector, the reactor comprising the combination of a membrane and a packing means, the packing means being disposed in the flow-through channel and effective for reducing band spreading of eluted sample bands in the liquid effluent, the membrane having an effective surface portion thereof selectively exposed in the channel for the purpose of an ion exchange suppression reaction with the effluent, or for the purpose of permeating reagent through the membrane into the channel for admixing with the effluent.

The invention as it further relates to liquid chromatographic apparatus, comprises in basic combination with the described reactor, the elements of an analytical column and a liquid chromatographic detector arranged in series with the reactor, whereby the effluent of the analytical column with sample bands resolved or partly resolved is passed through the flow-through channel of the reactor and outflowed ultimately to the detector to measure sample band(s) of interest in the effluent.

A further aspect of the invention relates to a method of liquid chromatographic analysis wherein generally sample is added to an analytical column and is displaced by liquid eluent, and the effluent of the analytical column with sample bands chromatographically resolved or partly resolved is passed to a detector through a reactor in which there is included a flow-through channel, whereby within the channel a suppression reaction or a reagent addition reaction is promoted to enhance the detection sensitivity of a sample band(s) of interest, the improvement which comprises using a packing means to reduce sample band spreading, the packing means being within the flow-through channel which receives the effluent and outflows the effluent ultimately to the detector, and in combination therewith, using a membrane having a surface portion which is selectively exposed in the flow-through channel for exchanging ions with the effluent for the purpose of the suppression reaction, or for permeating reagent through the membrane for admixing with the effluent for the purpose of the reagent addition reaction.

In respect to further details of the invention, the most preferred form of apparatus for suppression and reagent addition purposes both is a small tube membrane of about 500–1500 $\mu$I.D., and most preferably about 600–1000 $\mu$I.D., the bore of which is filled with a packing.

Liquid effluent of an analytical column is eluted into the bore of the packed tube membrane, wherein the effluent can enter into a suppression reaction at the inside surface of the tube, or be applied for the purpose of permeating a reagent through the wall of the tube to be physically admixed with the analytical column effluent.

The preferred membrane size range produces, in combination with proper particle sizes, low band spreading at acceptably low back pressures. While much larger tube membranes can also be designed to effectively produce very low band spreading, nondetrimental to high performance analytical columns, this is achieved typically at higher incurred levels of back pressure which may undesirably require a reinforcing jacket or other suitable reinforcement of the membrane.

Membranes useful for the suppression reaction are generally described as charged membranes which are molecularly porous. Ions of the opposite charge as the membrane tend to permeate selectively through the membrane whereas those of the same charge are rejected. These membranes are typically prepared by sulfonation (negatively charged membrane); or by amination (positively charged membrane) of various synthetic polymers, e.g., of ethylene. Particularly useful are sulfonated polyfluorocarbon membranes which are preferred because of excellent solvent resistance and ready commercial availability in useful sizes (sold under the trademark Nafion).

The term "suppression" or "suppressor" reaction, as used above, is intended to refer specifically to reactions distinctive to Ion Chromatography in which electrolyte eluent is converted to a weakly ionized form for the purpose of sensitively detecting sample ions in a weakly conductive background. Specific examples of common forms of useful suppressor reactions are given in Table I, below, wherein $R^-$ denotes the use of a negatively charged form of membrane; and $R^+$ a positively charged membrane.

TABLE I

| Eluent | Eluent Ion | Membrane/ Regenerant Suppressor Ion | Products of Reaction |
|---|---|---|---|
| Anion Analysis | | | |
| NaOH | $OH^-$ | $R^-H^+$ | $R^-Na^+ + H_2O$ |
| Na Phenate | $\phi O^-$ | $R^-H^+$ | $R^-Na^+ + \phi OH$ |
| $Na_2CO_3/NaHCO_3$ | $CO_3^{2-}/HCO_3^-$ | $R^-H^+$ | $R^-Na^+ + H_2CO_3$ |
| diNa—Glutamate | $Glut.^{2-}$ | $R^-H^+$ | $R^-Na^+ + R^-$ Glut.$H^+$ |
| Cation Analysis | | | |
| HCl | $H^+$ | $R^+OH^-$ | $R^+Cl^- + H_2O$ |
| $AgNO_3$ | $Ag^+$ | $R^+Cl^-$ | $R^+NO_3^- + AgCl \downarrow$ |
| $CU(NO_3)_2$ | $Cu^{2+}$ | $R\ NH_2$ | $R\ NH_2 \cdot Cu(NO_3)_2$ |
| Pyridine · HCl | $PyH^+$ | $R^+OH^-$ | $R^+Cl^- + Py + H_2O$ |
| Aniline · HCl | $\phi NH_3^+$ | $R^+OH^-$ | $R^+Cl^- + \phi NH_2 + H_2O$ |
| p-PDA · 2HCl | p-PDAH$_2^{2+}$ | $R^+OH^-$ | $R^+Cl^- + $ p-PDA $+ H_2O$ |

The charged membrane as used in the suppressor reaction is contacted on its surface remote from the analytical column effluent with a solution or slurry containing the ion form ($H^+$, $OH^-$, $Cl^-$, etc.) in order to continuously regenerate the membrane. Preferably, fresh regenerant solution is continuously supplied to this surface of the membrane at concentrations insufficient for breakthrough of the regenerant into the effluent, and sufficiently concentrated to completely neutralize or suppress the eluent. A regenerant may also be advantageously employed in the form of exchangeable ions ($H^+$, $OH^-$, $Cl^-$, etc.) attached to an ion exchange polymeric backbone. For example, acid or base form ion exchange resins, and particularly resins which are partially or completely dissolved in water, or an aqueous slurry may be used.

In respect to adding reagent to analytical column effluent, diverse known types of membranes (tubes or films) may be usefully employed to permeate selective chemically active species of the reagent. Particularly useful are porous cellulose membranes prepared such as by the method of U.S. Pat. No. 3,546,209. The permeation characteristics of cellulose membranes are generally that of size selection, and, accordingly, these may be broadly applied to permeate widely diverse reagent species. Synthetic polymeric membranes, such as produced typically from polyolefins and also silicone rubber, as well as a considerable group of other polymeric materials, may be additionally adapted for purposes of reagent addition. The latter membranes may be either charged or non-charged in type. For example, the charged membranes described for Ion Chromatography, supra, are useful for reagent addition, a specific embodiment thereof being described in Example 6, below. Membranes suitable for reagent addition are also described in U.S. Pat. Nos. 3,864,087; 4,025,308 and 4,131,428, which are referenced for further exemplary teachings useful in the selection of known selectively permeable membrane materials which may be fabricated into packed membrane structures for the applications intended by the invention.

The reaction kinetics of reagent addition methods, as well as prior developed reagents, are considered well known background technology to the invention and useful in its practice. For exemplary purposes only, specific examples of some of the very important reagent reactions useful in liquid chromatography, and specifically selected membranes for permeating these reagents are described by Davis, U.S. Pat. No. 4,448,691 incorporated fully herein by reference.

The importance of the packing means is generally viewed differently with respect to the suppression reaction, than in typical reagent addition methods. This is because in the suppression reaction, the high utility achieved is based on a combination of most importantly (1) radial transport (mixing) of the ionic solute to the membrane and thus greatly enhanced ion exchange efficiency allowing the use, e.g., of very short flow channels; and (2) closer duplication of small channel flow in large packed channels which effectively reduces band spreading in a manner which may be compared to using a series of very small channels (rather than a single large diameter channel) to reduce laminar flow forms of band spreading. Generally, it is frequently only the latter effect (2) which is predominantly important in reagent addition, thus permitting the use of much larger tube membranes (of other suitable flow channels) than previously considered feasible.

There are few technical reasons to use other than particle packing matrices since these work so satisfactorily and are amendable to simple fabrication procedures. However, the mixing effect (1) and small channeling effect (2) which reduces laminar form band spreading obviously may be duplicated by nonparticulate physical inserts. Somewhat practical forms of the latter packings would include sintered or open cellular structures which would not detrimentally produce dead flow spaces which would cause tailing. A small chain or an undulating wire would similarly produce mixing and occupy part of the core of the channel in such a manner to effectively reduce laminar flow band spreading effects.

INTENT CLAUSE

Nondetrimental forms of the above-described diverse packing means, to the extent literally construed as following within this term, are intended to be within the discovery upon which this invention is based and disclosed, and within the scope of the claims, below, or if not so covered, are intended to be covered as reasonably obvious equivalents, and are thus embraced within the scope of the invention by the application of the Doctrine of Equivalents upon which the inventors hereby intend to rely in constructing the fair scope of their inventive contribution.

THE DRAWING

Yet further objectives, aspects and advantages of the invention will in part be pointed out in, and in part apparent from, the following more detailed description of the invention considered together with the accompanying drawing, in which.

Figure 4:
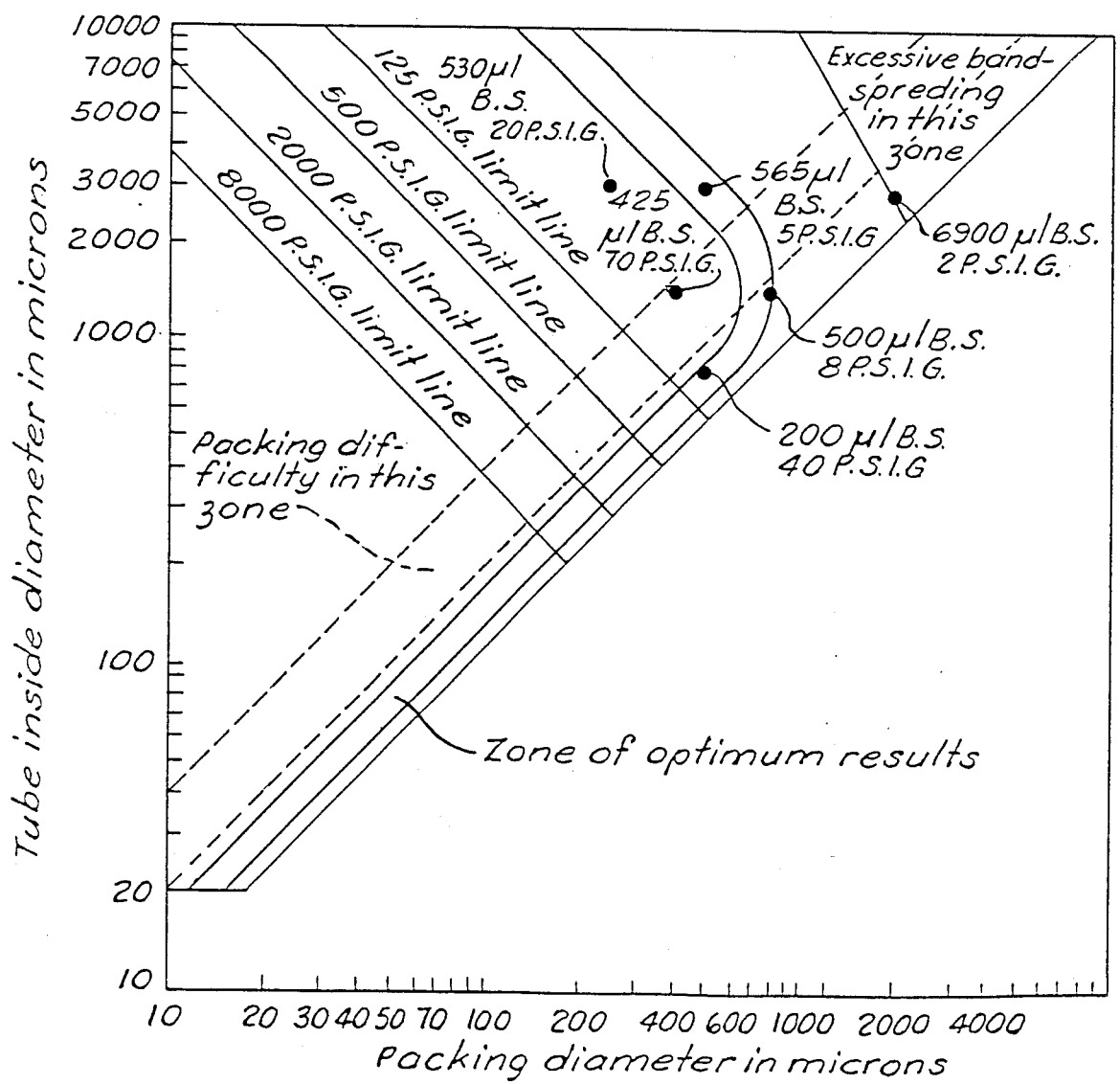
Figure 5:
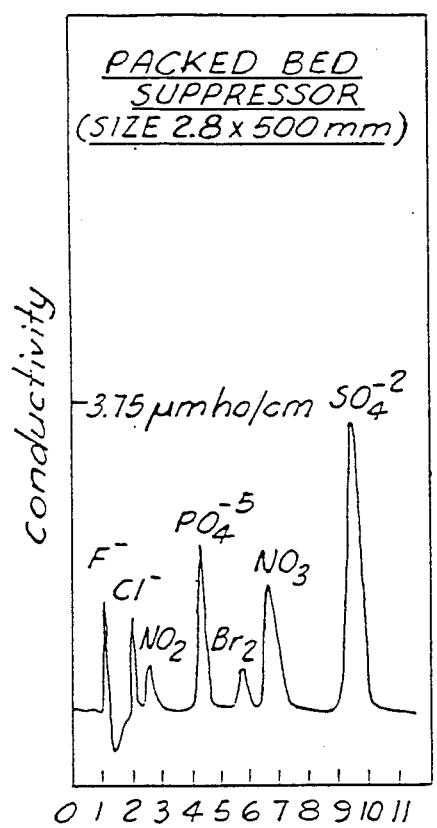
Figure 6:
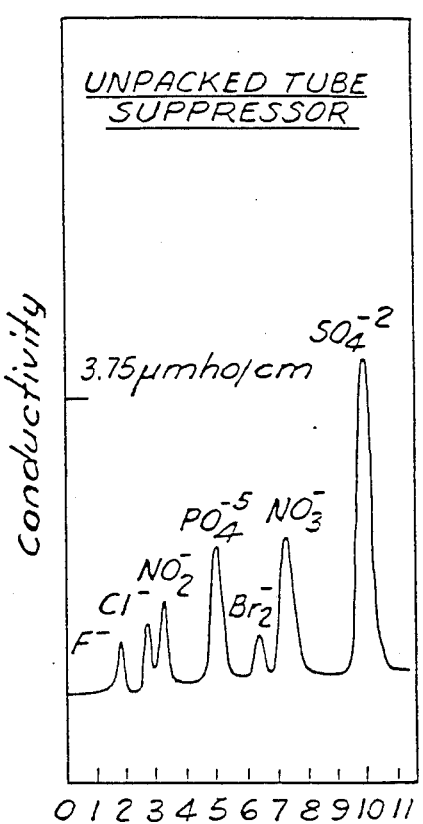
Figure 7:
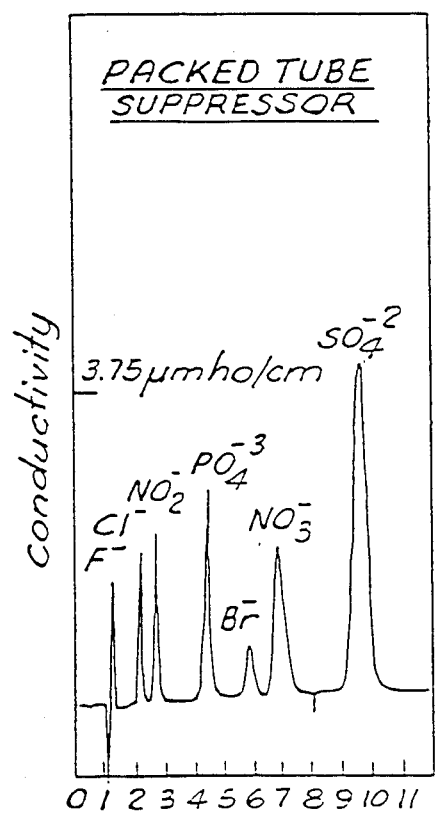

FIG. 4 is a graph which illustrates in respect to variables of tube membrane size, and packed particle size and type, approximate expected band spreading and back pressure values which would result at conventional liquid chromatographic use conditions; and FIGS. 5–7 are reproductions of chromatograms developed using the improved apparatus and method of the invention and using comparative prior art, and are associated with Example 2, below.

DETAILED DESCRIPTION OF THE INVENTION

Figures 1, 3:
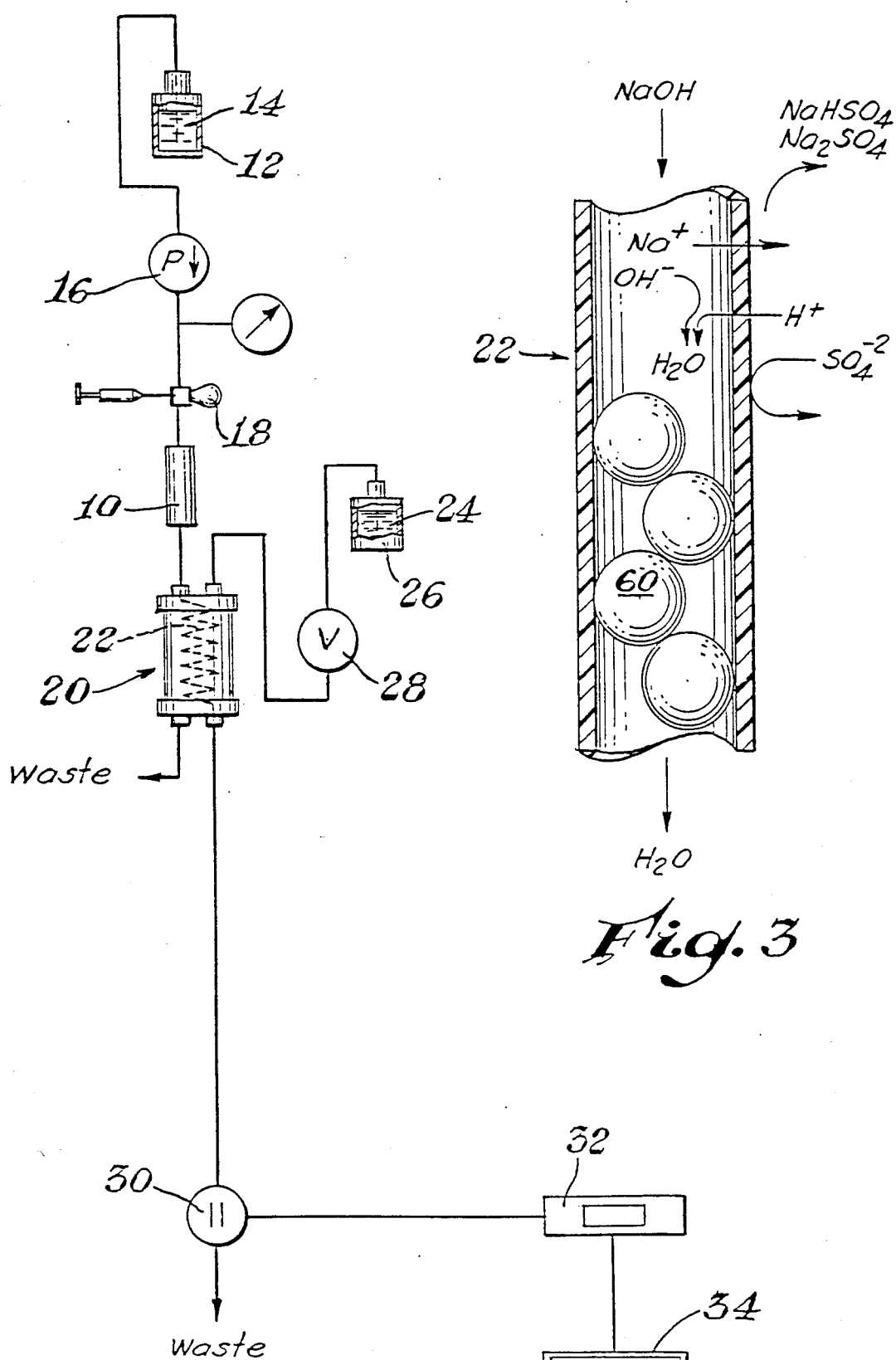
FIG. 1 is an elevational view of apparatus for performing liquid chromatography and which is constructed to employ the principles of the invention.
FIG. 3 is an enlarged cross-sectional view of a single tube membrane, such as may be used in the FIG. 2 device, and graphically illustrates the permselective ion transfer properties of the packed tube membrane which is relevant particularly to the Ion Chromatography suppressor reaction or a form thereof.

Referring to FIG. 1, there is shown a schematic view of liquid chromatographic apparatus which comprises a chromatographic or anlaytical column 10. The analytical column comprises a housed chromatographic separating means typically in the form of a particulate packing or gel through which sample is eluted to separate the sample into component species. Diverse types of separating means may be used to construct a suitable analytical column, as described extensively, e.g., by Snyder et al. In respect to Ion chromatography analysis, the analytical columns described in U.S. Pat. No. 3,966,596 and the high performance columns described by Stevens et al., U.S. patent application, Ser. No. 234,521, filed Feb. 2, 1981, now U.S. Pat. No. 4,383,047, would be preferentially selected.

Preferred means to add eluent or mobile phase to analytical column 10 comprises an eluent reservoir 12 containing eluent solution 14, the latter of which is withdrawn from the reservoir by a chromatographic pump 16 equipped with an optional pulse damping coil (not shown).

Preferred means for adding sample comprise, e.g., a syringe loadable sample injection valve 18. Sample added to the system at valve 18 is swept through the apparatus by the pumped eluent solution to chromatographic column 10. The sample elutes in the effluent of column 10, with component species thereof appearing chromatographically displaced in a background of the eluent or mobile phase.

A reactor/supressor device 20 includes a coiled packed membrane tube 22, into the bore of which the column 10 effluent is next fed. The opposite outer surface of the packed membrane tube is immersed in a stream of flowable regenerant/reagent 24 which is preferentially flowed counter to the flow of the effluent. The regenerant/reagent solution is supplied preferentially by gravity feed from a reservoir 26 through a flow control valve 28, and ultimately from device 20 to waste. The effluent stream emerges from the bore of the packed tube membrane chemically modified by the regenerant/reagent solution, and is ultimately fed in a continuous stream to a liquid chromatographic detector 30.

In the detector, the effluent produces an electrical signal proportional to the property monitored such as conductivity, light absorbance, fluorescence, etc., and which is directed from the detector ultimately to a suitable visual recorder 32, and simultaneously a chromatogram is produced using typically a strip chart recorder 34. An ion detector which is preferentially, a conductivity detector is used when the invention is to be applied to Ion Chromatography analysis.

Figure 2:
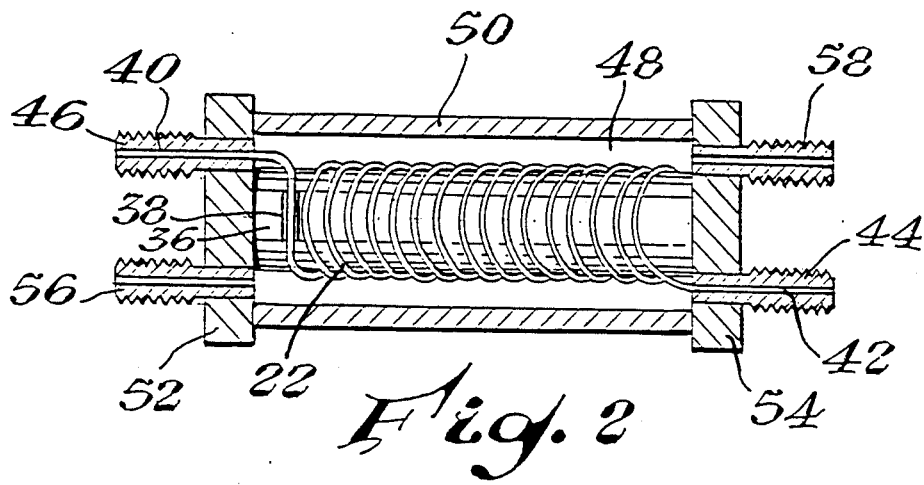
FIG. 2 is a cross-sectional view of the reactor device of the FIG. 1 apparatus.

Referring to FIG. 2, a preferred construction of the reactor/suppressor device is illustrated. The packed membrane tube 22, in this embodiment, is coiled about a supporting cylinder or mandrel 36 which is slotted as shown at 38. A short section of the membrane tube is pressed into the slot 38 and conformed to a flattened oval shape in order to form a bed support for the packing means, preferentially a particulate packing or particles 60 (shown in FIG. 3) to prevent them from dislodging or shifting position inside the tube. A simple tube clip could be substituted equivalently for slot 38 in these embodiments. The end portions 40, 42 of the packed membrane tube are inserted "dry" inside the bore of threaded eluent inlet and outlet ports 44, 46, respectively, and sealed by swelling the tube with water, or by use of suitable adhesive coatings. The tube membrane in this arrangement is preferentially packed with particles 60 from the region of effluent inlet port 44, forwardly to slot 38, the tube being unpacked with essentially little or no detrimental effect in the short section of the tube membrane which is forward of the slot.

An annular regenerant/reagent space 48 is defined immediately about mandrel 36 and is formed by a cylinder 50 which is arranged coaxially about the mandrel. End caps 52, 54 are joined to the contiguous ends respectfully of cylinder 50 and mandrel 36 which defines the thus enclosed regenerant/reagent space which communicates with reservoir 26 through a regenerant/reagent inlet port 56; and a waste collecting vessel (not shown) through regenerant/reagent outlet port 58.

FIG. 3 is a graphic illustration of the workings of the packed membrane tube as it can be beneficially applied as an improved suppressor device in an Ion Chromatography instrument. Dilute regenerant e.g., $H_2SO_4$ in water, is in contact with the outer wall of the packed membrane tube; and effluent composed, for example, NaOH eluent and sample are fed into the bore of the membrane tube. As the effluent flows through the bore of the membrane tube, it encounters active ion exchange sites on the inside surface of the tube (and/or on particles 60 as defined below), causing the $Na^+$ effluent ions to exchange with $H^+$ of the tube membrane, forming the product deionized water, in which the sample ions can be sensitively detected. The exchanged $Na^+$ ions are permeated ultimately through the wall of the tube membrane into the regenerant solution and swept away to waste; whereas, due to Donnon exclusion, the counter $OH^-$ ions are rejected. The $OH^-$ ions thus tend to remain in the effluent to form water with hydrogen ions of the regenerant which continuously recharge the active sites of the tube membrane. Similar suppression reactions can be envisioned with positively charged or aminated packed tube membranes to neutralize or suppress, e.g., HCl eluent ions with a $OH^-$ ion form regenerant. Essentially all the suppression reactions can thus be performed by devices using suitably one or the other of the above types of negatively or positively charged packed tube membrane structures.

Reagent addition methods differ from suppressor reactions in that the latter contemplate a balanced neutralizing of the effluent, while frequently excess reagent may be added to the effluent without detrimentally affecting the sensitivity of detection. This generally sets limits on the concentration of the regenerant at levels below that which would cause breakthrough of regenerant into the effluent and thus less sensitive detection. Immobile regenerant, such as attached to large polymeric molecules (for example, dissolved ion-exchange resin, or a slurry of ion exchange particles) can be used at increased regenerant concentration levels, however, since the large polymeric molecules would be non-permeable through the membrane wall.

In cases where regenerant or reagent concentration can be made suitably high, either because of the impossibility of membrane breakthrough or because an excess can be tolerated, large static or non-replenished reservoirs can be used in place of the illustrated device 20 using continuously fresh counter flowing regenerant or reagent solution.

When permitted, a static reservoir can thus be used wherein simply the packed tube membrane is immersed in a non-replenished solution of concentrated regenerant/-reagent which is preferably stirred to avoid a concentration differential from occurring and which would be replaced with fresh solution periodically. While the rejection properties of a membrane are not perfect, leaking effluent nevertheless would tend to produce only a very dilute amount of contaminant in a large concentrated reservoir of regenerant or reagent. Assuming that the contaminant is a possible interfering species, the effect, at most, may show only as a slightly varying baseline over a period of use. A suitable application for a static reservoir design is described particularly with respect to the teaching of Example 6.

The bore size of the tube membranes useful in the practice of the invention are broadly from about 20 to about 10,000 $\mu$I.D. Generally, similar dimensions apply for flat membrane structures, using the figure 10,000 $\mu$I.D. to refer to the minor diameter of the channels used in these devices as the outer broad limit of the invention. The void volume of such channels or bores is desirably less than about 20 ml.

The minimum dimension of 20 microns is approximately the current manufacturing limit of the art for hollow fiber manufacturing methods. The smallest size tube that can be used in this invention is determined essentially by the back pressure the tube can accept without being detrimentally affected. Since this is a function of liquid flow rate, extremely small tube membranes would be contemplated for use, e.g., in microbore chromatography described by Scott et al., J. of Chrom., Vol. 169, p. 51 (1979). In addition, since the invention can be practiced using several membrane tubes arranged in parallel, multiple small tubes can be used in these embodiments to overcome their back pressure limitations, as might preclude their use, for example, as a single tube membrane, as illustrated as the preferred embodiment.

The upper size limit of 10,000 $\mu$I.D. is arbitrarily set on the basis that a tube of too large an I.D. would incur the penalty of too much hold up volume and thus unnecessarily extend the time required for analysis.

The size of the packing particles also significantly affects back pressure values, and the amount of band spreading a given sized packed tube membrane will produce. Generally, the very large particles 60 and those which are very small, in relation to the bore size of the tube, will produce the highest amounts of back pressure. An optimum size thus exists between these levels which can be selected to maintain the back pressure acceptably low.

Band spreading, on the other hand, is generally invariably improved as the size of the particles is reduced in relation to the size of the tube. However, the improvement tends to become progressively less significant as the size of the particle is reduced. Thus, very definite optimum size levels may be selected in the intermediate size ranges, relating to bore size, where further gains in reducing particle size have little meaningful benefit in further reducing band spreading; and wherein the increased back pressure imposed by the addition of the packing means is within a very acceptable range. These optimum intermediate ranges of particle size where both desired minimal band spreading and acceptably low back pressure increase are realized vary depending on the specific size of the tube membrane or channel cross sectional area, as applies. Generally, the "intermediate" size range stated in relative terms to bore size (i.e., as a fraction thereof), narrows and tends to require the selection of smaller particles, relative to bore size, as the bore size is increased.

This phenomena is illustrated by the graph of FIG. 4. This graph should not be taken as applying in the absolute sense, since it assumes a given flow rate and membrane length. Particularly, the back pressure values shown in the graph would be shifted significantly at other than the assumed flow rate.

The plotted data points on this graph are taken from Example 1. From this plotted data, projections are made based on the assumption that a decrease in packing size by 4 times should reduce band spreading by two-fold, while incurring a 16-fold increase in back pressure, all other factors remaining constant. Hence, in moving diagonally toward the left corner of the graph, band spreading is generally improved, but at fast increasing rates of back pressure. At the value of about 200 $\mu$l band spreading, the effects are generally nondetrimental, and, hence, there is often little reason to pursue greater improvement. It is noted, nevertheless, that 200 $\mu$l is by no means the lower limit of achievable band spreading reduction, as this graph obviously would imply. It is also shown that for tube membranes in the preferential size range of about 600–1000$\mu$ bore diameter, an optimum choice of particles are those between about 0.6–0.8 as large as the bore diameter.

EXAMPLE 1

Suppressor devices are constructed for comparative testing using as the ion exchange membrane, commercial Nafion ® tube membranes available commercially from the the DuPont Company; and as the packing, generally spherical, inert beads of styrene-divinylbenzene copolymer. Bead size is carefully controlled using sieves, and by cropping only those beads which firmly lodge in the sieve openings. Microscopic examination shows the beads to have the same diameter ±5%. The beads are packed in preassembled or partly assembled suppressor devices by vacuum drawing or injecting into the eluent inlet port, a dilute slurry of the packing in deionized water containing a small amount of non-ionic surfactant (suitably 1% Brij 35). To evaluate relative band spreading performance, the devices are used with a Dionex Model 10 ion chromatograph with the analytical column removed; and the effluent inlet port of the suppressor device connected directly to the sample injection valve. Band spreading is determined, using chromatographic conditions of:

| | |
|---|---|
| Eluent: | 0.0024 M $Na_2CO_3$/ 0.003 M $NaHCO_3$ in deionized water at 160 ml/hr |
| Regenerant: | 0.02 N $H_2SO_4$ at 160 ml/hr. |
| Sample: | 50 $\mu$l of a solution of deionized water made up to contain in parts per million (ppm); 0.8 $F^-$, 1.0 $Cl^-$, 5.0 $NO_2^-$, 14 $PO_4^{-3}$, 2.5 $Br^-$, 8.5 $NO_3^-$, and 12.5 $SO_4$. |
| Detector Sensitivity: | 120$\mu$ mho/cm full scale. |

Band spreading is computed by injecting the sample standard and measuring the triangulated peak baseline width in $\mu$l. The sample injection volume (50 $\mu$l) is then subtracted to produce a measured value of band spreading also in $\mu$l. The data generated are shown in Table II.

TABLE II
Characteristics of Packed and Unpacked Tube Suppressors Capable of Suppressing a Maximum Eluent Flow of 160 ml/hr

| Device No. | Tube Internal Diameter, in $\mu$ | No. of Tubes | Tube Length Needed | Packing Diameter, In $\mu$ | Band Spreading In $\mu$l | Pressure Drop, In PSIG, for a Flow Rate of 160 ml/hr |
|---|---|---|---|---|---|---|
| 1 | 400[a,g] | 14 | 6[b] | None | 850 | ~2 |
| 2 | 800[c,g] | 1 | 20 | None | 870 | 6 |
| 3 | 800[c] | 1 | 5 | 500 | <200 | 40 |
| 4 | 1,400[d,g] | 1 | 20 | None | 5,000 | <1 |
| 5 | 1,400[d] | 1 | 5 | 850 | 500 | 8 |
| 6 | 1,400[d] | 1 | 5 | 425 | 400 | 70 |
| 7 | 3,100[e,g] | 1 | 20 | None | 33,000 | <1 |
| 8 | 3,100[e] | 1 | 8 | 2,000[f] | 6,900 | ~2 |
| 9 | 3,100[e] | 1 | 3 | 500 | 565 | 5 |
| 10 | 3,100[e] | 1 | 3 | 250 | 530 | 20 |

[a]Sulfonated polyethylene tube of Stevens et al. (Ser. No. 112,579)
[b]A bundle of tubes each 6 feet long.
[c]Nafion 811-X.
[d]Nafion 815-X.
[e]Nafion 810-X.
[f]2 mm stainless steel ball bearings.
[g]Comparative example The data of Table II indicate that the use of the packing results in much less membrane needed and much less band spreading. The improvements are greatest for the largest I.D. tubes used, Nafion 810-X. All of the packed devices, with the exception of Device No. 8, show less observed band spreading than the use of unpacked 400

μI.D., and 800 μI.D. tubes. The band spreading value for Device No. 8 considered to define the limit of marginally utility of devices constructed according to the invention; this data being plotted in FIG. 4 and appearing at about the limiting line drawn to define non-utility because of excessive band spreading.

EXAMPLE 2

The purpose of this example is to compare, under the same chromatographic conditions, the resolution efficiency of a Dionex Model 10 Ion Chromatograph instrument, which is equipped with a high performance analytical column and which is modified to use in these successive experiments; (a) a conventional ion-exchange resin bed suppressor column, 2.8×500 mm in size filled with Dowex 50 W×16 ion exchange resin in the hydrogen ion form, (b) an optimum form of unpacked tube membrane suppressor, being Device No. 2 of Table II, and (c) a packed tube membrane suppressor being Device No. 3 of Table II. The eluent and regenerant compositions and sample standard are the same as in Example 1. In each experiment, the same high performance analytical column is used and the same detector sensitivity is used, being 7.5 μmho per cm full chart deflection.

FIG. 5 is a reproduction of the chromatogram obtained when the conventional suppressor column is used. FIG. 7 is a reproduction of the chromatogram obtained when the packed tube membrane suppressor of the present invention is used. Note the improved resolution of the peaks in FIG. 7 especially the resolution of $Cl^-$ and $NO_2^-$ and of $Br^-$ and $NO_3^-$ vs. the peaks in FIG. 5. The $NO_2^-$ peak is taller in FIG. 7 because band spreading is less with the present invention and because $NO_2^-$ partially reacts with the ion-exchange resin in the conventional suppressor column, removing it from the eluent stream so that less $NO_2^-$ ion passes to the detector. FIG. 6 is a reproduction of the chromatogram obtained when the unpacked tube membrane suppressor is used. Comparing FIG. 6 with FIG. 7, note again the superior resolution efficiency of the present invention due to the reduced band spreading. This superiority is evidenced by sharper peaks and better resolution especially of $Cl^-$ and $NO_2^-$ and $Br^-$ and $NO_3^-$. Also, the peaks are taller in FIG. 7 resulting in superior detection sensitivity.

EXAMPLE 3

The purpose of this example is to demonstrate a packed tube membrane suppressor for cation analysis using Ion Chromatography. The device is constructed using as the membrane, a tube membrane of aminated Microline ® (Product Code 1850, Thermoplastics Scientific, Inc.), aminated by the RAI Research Corp. according to the procedure outlined by V. D'Agostino et al., *Proceedings of the Electrochemical Society*, Vol. 81-2 (1981). The tube is packed with 500μ styrene-divinylbenzene copolymer beads according to the procedure of Example 1. Dow Corning Room Temperature Vulcanizing Silicone Rubber Bath Tub Caulk is used to seal the tubing ends in the eluent inlet and outlet ports. The device is used with a Dionex Model 10 Ion Chromatograph instrument equipped with a 9×100 mm analytical column filled with 50μ surface sulfonated styrene-divinylbenzene copolymer prepared according to U.S. Pat. No. 3,966,596. The eluent is 0.01M HCl at a flow rate of 160 ml per hour. The suppressor device is regenerated with 0.02M NaOH at a flow rate of 160 ml per hour. The detector sensitivity is set at 30 μmho per cm full chart deflection. The recorder baseline is smooth and flat at the low conductivity value of about 16 μmho per cm indicating an efficient suppression of the much higher conductivity of the eluent. 50 μl of a solution containing 100 ppm $Na^+$ and 170 ppm $K^+$ is injected. The recorder shows a normal Gaussian peak for $Na^+$ at 4.5 minutes being about 29 μmho per cm tall and a normal Gaussian peak for $K^+$ at 7.5 minutes being about 18 μmho per cm tall. At 10 minute intervals, 5 serial dilutions of the sample standard are injected with the final dilution containing 2.5 ppm $Na^+$ resulting in a peak 0.63 μmho per cm tall; and containing 4.25 ppm $K^+$ resulting in a peak 0.31 μmho per cm tall. A plot of concentration of $Na^+$ and $K^+$ vs. peak height produces a smooth curve that is nearly linear. The band spreading of the device is determined to be 200 μl. This example clearly demonstrates the utility of a packed tube membrane suppressor for cation analysis by Ion Chromatography. Conventional ion-exchange resin filled suppressor columns result in more band spreading (usually about 500 μl) and since they exhaust in use, must be periodically regenerated. Regenerating a suppressor column for cation analysis by Ion Chromatography is much more difficult than regenerating one for anion analysis because the regenerated suppressor for cation analysis requires extensive rinsing with water to obtain a smooth and steady baseline, often taking several hours to as much as a day. All of the above problems with the conventional ion-exchange resin filled suppressor column are greatly minimized by the use of the present invention.

EXAMPLE 4

The purpose of this example is to compare, under the same chromatographic conditions, the effect of placing sulfonated packing into a cation-exchange tube membrane suppressor. Four devices are constructed, each containing a tube of Nafion 811-x 2.5 feet long, and using as the packing: (A) unsulfonated 500μ styrene-divinylbenzene copolymer beads; (B) surface sulfonated 500μ styrene-divinylbenzene copolymer beads having a cation exchange capacity of 0.01 Meq per gram; (C) surface sulfonated 500μ styrene-divinylbenzene copolymer beads having a capacity of 0.8 Meq per gram (both of the above surface sulfonations are performed according to U.S. Pat. No. 3,966,596); and (D) 500–580μ Dowex ® 50W×4 Ion Exchange Resin having a cation exchange capacity of about 5.2 Meq per gram. Device A suppresses a maximum eluent flow rate of 80 ml per hour; Devices (B) and (D) a maximum eluent flow rate of 112 ml per hour; and Device (C), a maximum eluent flow rate of 138 ml per hour. The band spreading of Devices (A), (B) and (D) is 170 μl; and that of Device (C) is 230 μl. When examined under a microscope, the packing of Devices (A), (B) and (D) appeared to be smooth spheres, while the packing of Device (C) appeared to be spherical but rough not unlike a ball of twine. All of the sulfonated packings increased the maximum eluent flow rate that could be suppressed. The use of the roughly surfaced packing of Device (C) increased the maximum eluent flow rate but also increased band spreading to an extent that its overall performance is judged to be inferior. No significant difference in performance is seen between the 0.01 Meq per gram packing and the 5.2 Meq per gram packing. This example illustrates that for packed cation exchange tube membrane suppressors, best overall performance is seen when the packing is sulfonated and its surface remains smooth and spherical.

EXAMPLE 5

The purpose of this example is to compare packed and unpacked flat membrane suppressors. An Amicon CEC-1 Post Column Concentrator, modified for counter-current flow of regenerant, is used as a flat membrane form suppressor and is fitted with a sheet of Nafion ® 117 ion exchange membrane film. The eluent is directed through the spiral channel of the upper plate being 280µ deep, 3200µ wide and 4 feet long. The unpacked device suppresses a maximum eluent flow rate of 16 ml per hour and shows a band spreading value of 675 µl. In packed form, using 250µ styrene-divinylbenzene beads, the device suppresses a maximum eluent flow rate of 48 ml per hour and has a lesser band spreading value of 300 µl. Thus, the packing of the eluent channel of a flat membrane suppressor significantly reduces band spreading and at the same time greatly increases the maximum eluent flow rate.

EXAMPLE 6

The purpose of this example is to demonstrate the utility of the present invention for the important application of post column derivatization. The device is six inches of Nafion 810-X ion exchange tubing having an internal diameter of about 3100 microns containing a packing of 30-40 U.S. Mesh size glass beads. The application and experimental conditions are the same as in Davis, U.S. Pat. No. 4,448,691, Example 2, except that the device of the present invention is used. A comparison of chromatograms generated with the present invention and generated with the invention of the above cited U.S. patent shows only minor differences with slightly taller peaks observed with the use of the present invention.

The important advantage of the present invention vs. the above cited U.S. patent is that much larger tubes can be used with the present invention. The above cited U.S. patent is limited to "hollow fibers", i.e., limited to internal tube diameters of a maximum size of 1,000 microns because excessive band spreading is observed with the use of tube diameters greater than 1,000 microns. The present invention solves this problem and allows the use of tubes of an internal diameter larger than 1,000 microns because band spreading is not excessive and indeed is less with the present invention. The use of the larger tubes possible with the present invention is an advantage when (a) only larger tubes are available, (b) because larger tubes are often easier to connect into the system and (c) because larger tubes are often physically stronger and thus considerably more durable.

What is claimed is:

1. In an improved liquid flow-through reactor in which there is included a flow-through channel, wherein the improvement comprises the combination of a membrane and a packing means, the membrane having a surface portion thereof selectively exposed in the channel, the packing means positioned in the channel and being effective for controllably reducing extra column bandspreading in the reactor relative to bandspreading of the same reactor without the packing means, the bandspreading with the packing means being about 500 µl or less, the packing means being contiguous with the portion of the flow-through channel exposed to the membrane.

2. The reactor of claim 1 comprising a tube membrane and as the packing means, particles packed in the bore of the tube membrane.

3. The reactor of claim 2 wherein the membrane consists of a single tube membrane having an inside diameter of between about 500-2000 microns.

4. The reactor of claim 3 in which the single tube membrane has a bore diameter of between about 600-1000 microns and wherein the packing means comprise particles which are generally spherical and have a diameter which is between about 0.6-0.8 as large as the bore diameter.

5. An ion chromatographic analytical instrument comprising as the suppressor device, the reactor of claim 1 having a charged membrane, and which comprises in combination with the suppressor device, the elements of an ion-exchange analytical column and a liquid chromatographic ion detector arranged in series with the suppressor device, whereby the effluent of an analytical column with sample bands resolved or partly resolved is passed through the flow-through channel of the suppressor device and out-flowed ultimately to the detector to measure simple band(s) of interest in the effluent.

6. The instrument of claim 5 wherein the suppressor device defines a flow-through regenerant space contacting the surface portion of the membrane opposite its surface portion selectively exposed in the flow-through channel.

7. The instrument of claim 6 comprising as the membrane, a charged membrane tube.

8. The instrument of claim 7 comprising as the membrane, a tube membrane having a bore diameter of between about 500-2000 microns, and as the packing means, particles packed in the bore of the tube membrane.

9. The instrument of claim 8 comprising a membrane consisting of a single tube of between about 600-1000 microns bore diameter, and wherein the packing means comprise generally spherical particles between about 0.6-0.8 as large as the bore diameter.

10. The instrument of claim 5 comprising the combination of a charged membrane and packing means effective for reducing extra column band spreading to about 300 µl or less.

11. The instrument of claim 5 comprising an ion exchange packing means of the same charge as the charged membrane.

12. Apparatus for liquid chromatographic analysis using post-column reagent addition and which comprises as the post-column reactor, the reactor of claim 1, and which comprises in combination with the reactor, the elements of an analytical column and liquid chromatographic detector arranged in series with the reactor, whereby the effluent of an analytical column with sample bands resolved or partly resolved is passed through the flow-through channel of the reactor and outflowed ultimately to the detector to measure sample band(s) of interest in the effluent.

13. The apparatus of claim 12 wherein the reactor defines a static reservoir receiving space contacting the surface portion of the membrane opposite its selectively exposed surface portion exposed in the flow-through channel.

14. The apparatus of claim 12 comprising as the membrane, a reagent permeable tube membrane, the bore diameter of which is greater than 1000 microns.

15. The apparatus of claim 12 comprising a flow-through channel which in minor diameter is greater than 1000 microns.

16. The apparatus of claim 12 comprising a membrane consisting of a single reagent permeable tube membrane, the bore of which comprises the flow-through channel, and which contains particles as the packing means.

17. The apparatus of claim 12 comprising the combination of a membrane and packing means effective for reducing extra column band spreading to about 300 μl or less.

18. The reactor of claim 1 comprising the combination of a membrane and packing means effective for reducing extra column band spreading to about 300 μl or less.

19. In an improved method of analysis comprising adding a sample, composed of at least one component, to a flowing stream of liquid passed through a reactor to a detector, the reactor includes a flow-through channel which receives the liquid and outflows the liquid eventually to the detector, whereby within the channel a suppression reaction or a reagent addition reaction is promoted to enhance detection sensitivity of at least one component of the added sample, wherein the improvement comprises using a membrane having a surface portion which is selectively exposed in the flow-through channel for exchanging ions with the liquid for the purpose of the suppression reaction, or for permeating reagent through the membrane for admixing with the liquid for the purpose of the reagent addition reaction, and using a packing means to controllably reduce extra column bandspreading of the reactor, the reactor of the method beneficially providing low extra column bandspreading in the reactor of about 500 μl or less, the packing means being contiguous with the portion of the flow-through channel exposed to the membrane.

20. The method of claim 19 using the method for the suppressor reaction in ion chromatography.

21. The method of claim 20 using as the membrane an ion-exchange membrane tube the bore of which defines the flow-through channel, and using as the packing means particles packed in the bore of the tube membrane.

22. The method of claim 21 using a tube membrane having a bore diameter of between about 500–2000 microns.

23. The method of claim 22 using a tube membrane the bore diameter of which is between about 600–1000 microns, and which is packed with generally spherical particles as the packing means, the particles having a diameter of between about 0.6–0.8 as large as the bore diameter.

24. The method of claim 19 using the method for liquid chromatographic post-column reagent addition.

25. The method of claim 24, the improvement which comprises using a packing means to reduce extra column band spreading to about 300 μl or less.

26. The method of claim 24 using a flow-through channel of greater than 1000 microns minor diameter.

27. The method of claim 26 using as the membrane, a reagent permeable tube membrane the bore of which defines the flow-through channel.

28. The method of claim 27 using as the packing means, generally spherical particles packed in the bore of the tube membrane.

29. The method of claim 20, the improvement which comprises using a packing means to reduce extra column band spreading to about 300 μl or less.

30. The method of claim 29 using a charged membrane and an ion exchange packing means of the same charge as the membrane.

* * * * *

UNITED STATES PATENT AND TRADEMARK OFFICE
CERTIFICATE OF CORRECTION

PATENT NO. : 4,751,004

DATED : June 14, 1988

INVENTOR(S) : Timothy S. Stevens, Gary L. Jewett; Robert A. Bredeweg

It is certified that error appears in the above-identified patent and that said Letters Patent is hereby corrected as shown below:

Col. 4, line 11, the first word should be capitalized to read -- "Regenerant" --.

Col. 6, Table I, delete the word "Suppressor" from the heading of the third column and insert -- Suppressor -- before "Reaction" in the heading of the fourth column so that the heading reads -- Products of Suppressor Reaction --.

Col. 8, line 26, "anlaytical" should read -- analytical --.

Col. 9, line 43, insert -- of -- before "NaOH";

line 49, insert -- ions -- before "of".

Col. 13, line 2, insert -- is -- before "considered";

line 43, insert -- of -- before "$Br^-$".

Signed and Sealed this

Third Day of January, 1989

Attest:

DONALD J. QUIGG

*Attesting Officer*  *Commissioner of Patents and Trademarks*